United States Patent
Pedrazzini

(10) Patent No.: US 8,397,473 B2
(45) Date of Patent: Mar. 19, 2013

(54) APPARATUS FOR CLOSING BIOLOGICAL MATERIAL CONTAINERS

(75) Inventor: Gianandrea Pedrazzini, Paradiso (CH)

(73) Assignee: INPECO IP Ltd., Valletta (MT)

( * ) Notice: Subject to any disclaimer, the term of this patent is extended or adjusted under 35 U.S.C. 154(b) by 164 days.

(21) Appl. No.: 12/809,540

(22) PCT Filed: Dec. 15, 2008

(86) PCT No.: PCT/EP2008/067570
§ 371 (c)(1),
(2), (4) Date: Aug. 20, 2010

(87) PCT Pub. No.: WO2009/080594
PCT Pub. Date: Jul. 2, 2009

(65) Prior Publication Data
US 2010/0307109 A1 Dec. 9, 2010

(30) Foreign Application Priority Data
Dec. 20, 2007 (IT) .............................. MI2007A2396

(51) Int. Cl.
*B65B 7/28* (2006.01)
(52) U.S. Cl. ............................ 53/317; 53/307; 53/331.5
(58) Field of Classification Search .................... 53/505, 53/306, 307, 317, 331.5, 310
See application file for complete search history.

(56) References Cited

U.S. PATENT DOCUMENTS

| | | | | |
|---|---|---|---|---|
| 1,857,075 A * | 5/1932 | Wright et al. | ...................... | 53/71 |
| 3,975,886 A * | 8/1976 | Waters | ............................. | 53/310 |
| 4,674,263 A * | 6/1987 | Kelly | ............................... | 53/317 |
| 4,696,144 A * | 9/1987 | Bankuty et al. | ............... | 53/331.5 |
| 4,850,470 A * | 7/1989 | Ferkany | ...................... | 198/345.3 |
| 4,870,806 A * | 10/1989 | Sprenger | ......................... | 53/485 |
| 4,928,453 A * | 5/1990 | Ferkany et al. | .................... | 53/67 |
| 5,150,558 A * | 9/1992 | Bernhard | ......................... | 53/167 |
| 5,157,897 A * | 10/1992 | McKee et al. | .................... | 53/308 |
| 6,430,896 B1 * | 8/2002 | Torikian | ........................... | 53/310 |
| 6,494,017 B1 * | 12/2002 | McGrath et al. | ................... | 53/53 |
| 2005/0284102 A1 * | 12/2005 | Herzog | ............................. | 53/75 |

FOREIGN PATENT DOCUMENTS

GB 2228729 A 9/1990

* cited by examiner

*Primary Examiner* — M. Alexandra Elve
*Assistant Examiner* — Andrew M Tecco
(74) *Attorney, Agent, or Firm* — Birch, Stewart, Kolasch & Birch, LLP

(57) ABSTRACT

An apparatus for automatically closing test tubes containing biological material mounted to an automatic test tube conveyor is described, comprising a cap recruiting device (11) adapted to feed a curved channelizer (12) adapted to tip a cap (5) from a configuration with the opening upwards at the inlet of the channelizer (12) to a configuration with the opening downwards at the outlet of the channelizer (12) at a loading surface (13). A horizontal pusher (22) moves the cap (5) from said loading surface (13) to a housing (23) in a channel (14) in which a stem (24) vertically slides and is adapted to move the cap (5) upwards in a test tube closing device (9) comprising a movable head (26) adapted to grip the cap (5) pushed by the stem (24) and to close the open test tube blocked at a working point of the conveyor.

4 Claims, 5 Drawing Sheets

APPARATUS FOR CLOSING BIOLOGICAL MATERIAL CONTAINERS

The present invention relates to an apparatus for closing biological material containers.

Biomedical scientific progress, on one hand, and technological developments, on the other, caused a remarkable development in laboratory medicine, with a continuously increasing number of tests required for outpatients, hospitalized patients, and for each hospitalization.

Laboratory medicine addressed the organizational and economic challenges deriving from such a rapid growth by using automation, with the purpose of reducing personnel cost, speeding up test times and improving test quality at the same time, in virtue of the features of better precision and accuracy of the automated processes. Once restricted to a few tests requested with particular frequency, and influenced by test methods much less refined than today's, automation has thus rapidly evolved, in virtue of the evolution of the test methods and progresses in electronics, sensors, computers, etc. This transformation had a major impact on the increase in test request.

The following objects are essentially pursued in the constant push to reduce costs and increase test quality:
  increasing efficiency of the testers used for testing;
  consolidating different technologies (e.g. immunochemistry and clinical biochemistry) on the same testing machine;
  using technologies adapted to automate and integrate the steps of pre-testing, testing and post-testing in a single working chain.

As biomedical process makes a continuously increasing number of tests available to laboratory medicine, the correct, fast and safe management of the biological material specimens to be tested is becoming increasingly more important.

We assume the case in which the biological specimen to be tested is blood, previously collected from a patient and contained in specific containers, named test tubes.

With regard to the step of pre-testing, the preparation which is carried out on the blood specimens to be tested, consists of various actions such as centrifugation, removal of the closure adapted to seal the test tube, distribution of the blood contained in a test tube into several test tubes (aliquoting) and possible subsequent closing of the test tubes cloned from the original test tube so as to allow the transportation thereof, if needed, outside the laboratory to other laboratories or hospital departments.

The automation of the handling operations which need to be carried out on a biological material specimen does not simply consist in automating such actions one by one, but instead automation means performing a working cycle, from preparing to testing, and to subsequently storing the specimens, in a completely automatic manner. This means implementing a process in which the laboratory operator is manually involved only in the initial step of the process, in which the test tubes must be introduced into the automation cycle. Once such an operation has been performed, all actions are automatically and dynamically performed on the specimen by using appropriate software programs adapted to actuate and control a correct lifecycle of the specimen introduced into an automation chain.

One of the actions performed on the specimen includes closing the test tubes by appropriate caps, after the aliquoting process of a test tube containing biological material. In detail, aliquoting is a process which includes extracting the specimen from a test tube and distributing the same into several test tubes. The object of this action is to obtain several containers containing the same biological material on which different tests may be performed at the same time, possibly in different laboratories. If the transportation of such containers is provided, an appropriate closing must be ensured so as to ensure the integrity of the specimens during the transportation.

It is the object of the present invention to make an apparatus adapted to automatically close test tubes using caps and seals suitable for this purpose, inserted into a global automation context, so as to overcome the above-described problems.

In accordance with the invention, the object is achieved by an apparatus for automatically closing test tubes containing biological material, which is mounted to an automatic test tube conveyor, characterized in that it comprises a cap recruiting device adapted to feed a curved channelizer adapted to tip a cap from a configuration with the opening upwards at the inlet of the channelizer to a configuration with the opening downwards at the outlet of the channelizer at a loading surface, a horizontal pusher moving the cap from said loading surface to a housing in a channel in which a stem vertically slides and is adapted to move the cap upwards in a test tube closing device comprising a movable head adapted to grip the cap pushed by the stem and to close the open test tube blocked in a working point of the conveyor.

These and other features of the present invention will be further apparent from the following detailed description of a practical embodiment thereof shown by way of non-limitative example in the accompanying drawings, in which:

FIG. 1 shows an apparatus adapted to automatically close test tubes mounted to a conveyor 1 adapted to automatically transport test tubes 2 containing biological material specimens.

Figure 1:
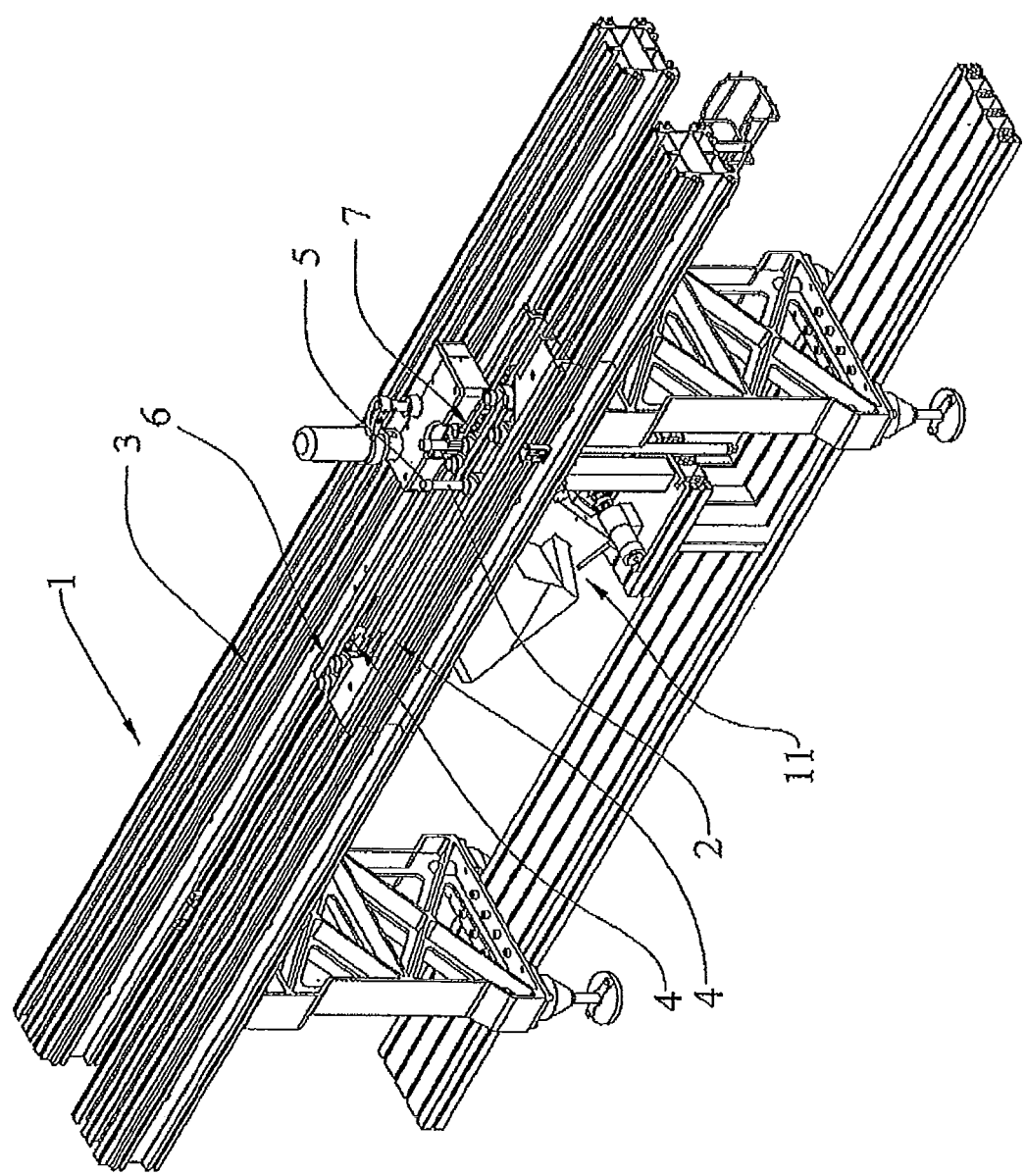
FIG. 1 shows a perspective view of the apparatus for automatically closing test tubes, included in the conveyor adapted to automatically transport biological material test tubes.

Said conveyor 1 consists of a conveyor belt 3 responsible for the automatic transport of test tubes 2 to further processing and testing modules for the biological material specimens. Such a conveyor belt 3 comprises main and secondary lanes 4 serving the function of conveying test tubes to the processing and testing modules, as described in Italian patent application MI2007A002254.

The transport of test tubes on said conveyor belt 3 is allowed by the use of appropriate test tube transporting devices 6 which ensure the verticality and stability of the test tubes when processing them. Such transporting devices 6 are appropriately diverted and stopped on the conveyor belt by means of specific stopping and diverting devices included in the conveyor 1.

The test tubes transported by the conveyor 1 which need to be closed with suitable cylindrical caps 5 are conveyed onto the interfacing lane 4 by the described apparatus and stopped at a working point 7.

At such a working point 7, the test tube 2 may be stopped and it is possible to operate thereon by keeping a stable, vertical position thereof.

Figure 2:
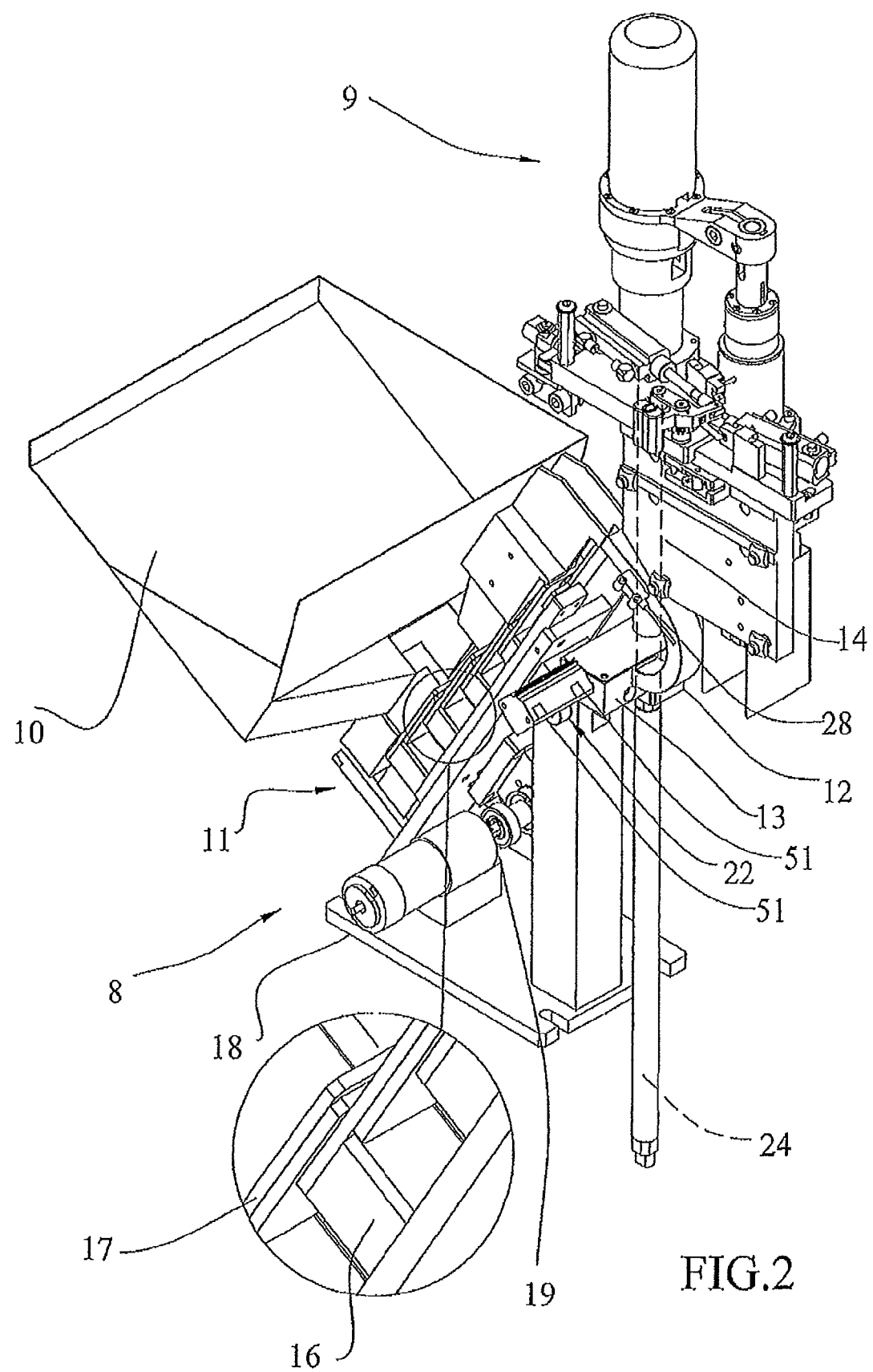
FIG. 2 shows a perspective view of the apparatus for automatically closing test tubes, removed from the conveyor adapted to automatically transport test tubes.

The apparatus adapted to automatically close test tubes consists of two main devices: a cap recruiting and loading device 8 and a test tube closing device 9 (FIG. 2).

The cap recruiting and loading device 8 comprises a cap container 10 adapted to contain the caps to be used during the working cycle, which caps are conveyed from a recruiting device 11 through a channelizer 12 into a loading chamber 13 and then into a channel 14 communicating with the test tube closing device 9 (FIG. 2).

Said recruiting device 11 consists of fixed combs 16 and movable combs 17. The movable combs 17 move (as shown by the arrows in FIG. 4) on the fixed combs 16, thus moving the caps 5 upwards.

The caps 5 engaged in such a recruiting mechanism reach the top of the device only if, when engaged by the container 10, they rest on the combs on the closed side. If they are engaged by the rising mechanism in a reverse position, they fall because they are unbalanced with respect to their centre of gravity: this is due to the inclination of the recruiting device 11 (preferably of 60° for cylindrical caps with a radius of 8 mm, height of 9 mm and thickness of 0.9 mm), which ensures that the caps are only recruited in the desired position, i.e. so that they are fed into the channelizer 12 with the cap opening upwards, the path of the channelizer 12 reversing such a configuration. The dimensions of the channelizer 12 are substantially complementary to those of the cap 5 so as to avoid unexpected tipping of the cap 5 which is able to either move along the channelizer 12 or rotate about its axis.

Figure 4:
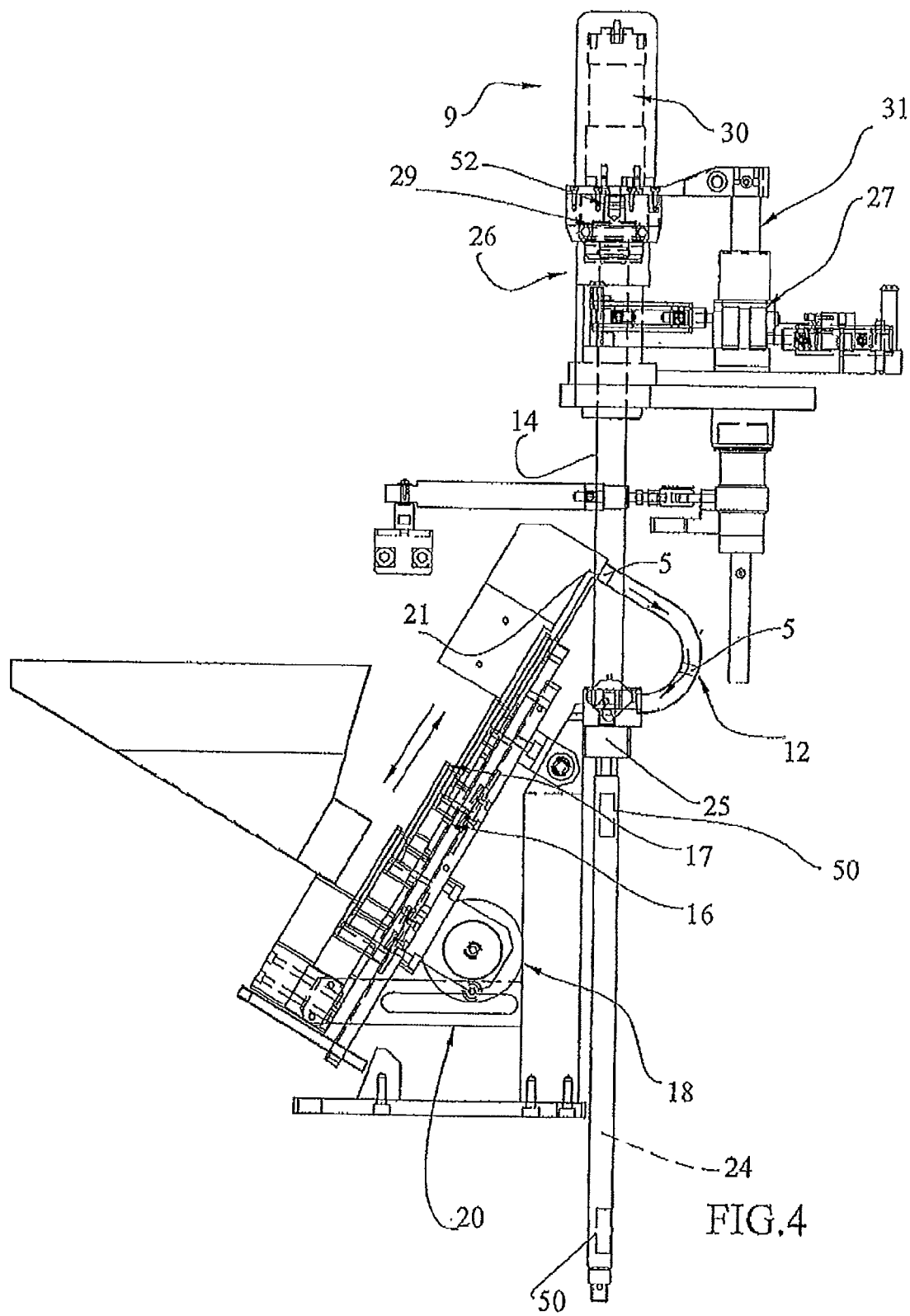
FIG. 4 shows a side view of the configuration in FIG. 2.

The movable combs 17 are moved by an electric motor 18 which, by means of a driving system 19, moves a movable arm 20, thus generating the stroke of the movable combs 17 on the fixed combs 16 (FIGS. 2 and 4).

Figure 3:
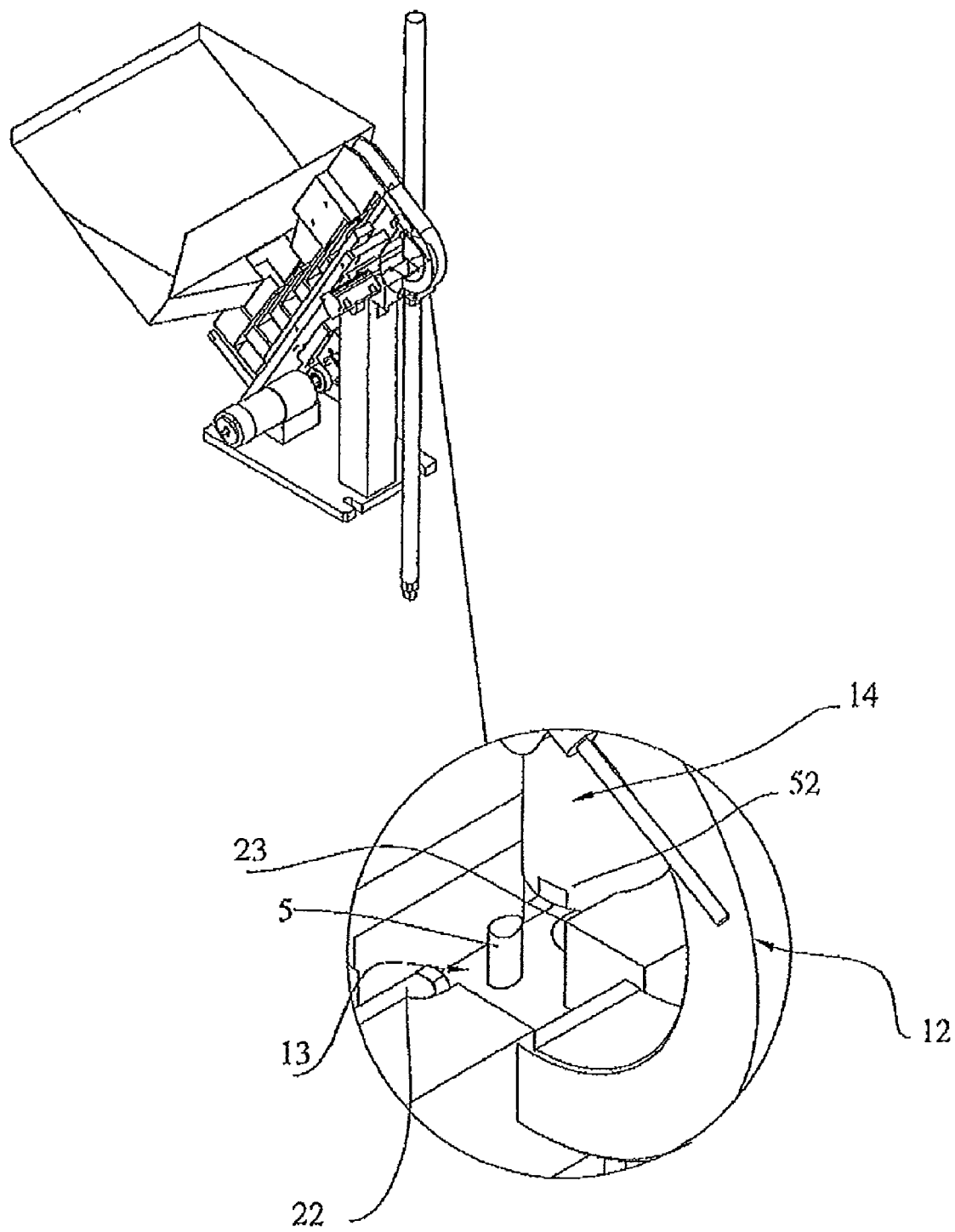
FIG. 3 shows a perspective view of a detail of the cap recruiting and loading device.

Once the highest comb 21 (FIG. 4) of the recruiting device 11 has been reached, the cap follows a compulsory path along the channelizer 12 and such a travel ends, as previously mentioned, in the loading chamber 13 (FIG. 3).

During the compulsory path in the channelizer 12, the cap follows a curved, downward course, and reaches the loading chamber 13 in a position opposite to the recruiting position; this is the correct position of the cap on the test tube, i.e. with the cap opening downwards.

A cylinder or horizontal pusher 22 moves the cap, into the loading chamber 13, under the opening of the channel 14, into the housing 23 (FIGS. 2 and 3).

Inside the channel 14, there is a stem 24 (FIG. 4), provided with a pusher 25, which by engaging the cap present in the housing 23, pushes it into the channel 14 to the head 26 of the test tube closing device 9. The stem 24 is provided with a pair of magnetic sensors 50 (the positions of said sensors inside the cylinder are shown in FIG. 4), adapted to detect the current position of the cylinder itself: "low" position when both magnets are activated and "high" position when only the upper magnet is activated. In the high position, the housing 23 is engaged by the presence of the stem 24, and thus the cylinder 22 may not move the cap into the housing 23; in the low position, the cylinder 22 may work and move the cap into the housing 23.

A further pair of magnetic sensors 51 (the positions of said sensors in the cylinder are shown in FIG. 2) is present also in cylinder 22 to monitor the current position of the cylinder itself: the "in" position when both magnets are activated and the "out" position when only the outermost magnet is activated.

A slot is present on the channelizer 12 on which a presence sensor 28 is installed (FIG. 2) adapted to monitor the presence of caps 5 inside the channelizer 12, and possibly to manage the operation of the cap recruiting and loading device 8: if the presence sensor 28 signals the presence of caps in the channelizer, the comb system 15 will stop until a counter order is received from the sensor.

A further presence sensor 52 (FIG. 3) is included inside the channel 14, close to the housing 23, for ensuring the presence of a cap 5 during the operations.

The device adapted to close the test tubes 9 (FIG. 4) is functionally equivalent to the device described in international patent application PCT/EP2006/069251, except for the head 26 adapted to grip a cap 5 provided by the cap recruiting and loading device 8 by means of the channel 14, as previously described.

Inside the head 26, there is a chamber 29 rotated by an electric motor 30 placed inside the head. When the pusher 25 reaches the chamber 29, the cap 5 is kept housed inside the chamber by snapping. A presence sensor 52 inside the head signals the presence of the cap, thus allowing the test tube closing device 9 to start the working cycle.

Figure 7:
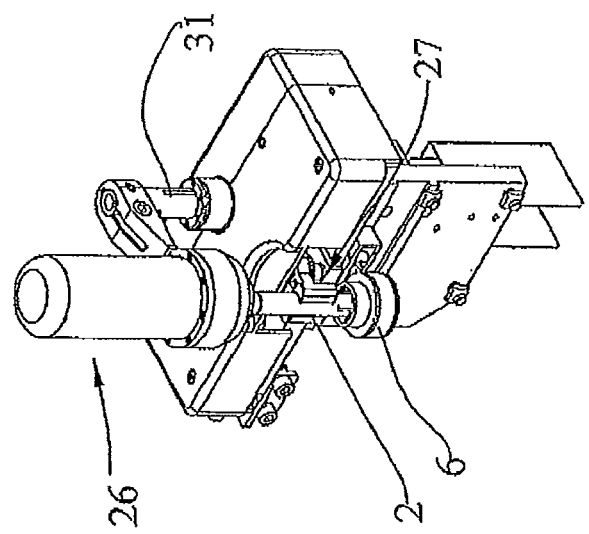
FIG. 7 shows the test tube closing device in a configuration which follows that of FIG. 6.
Figure 6:
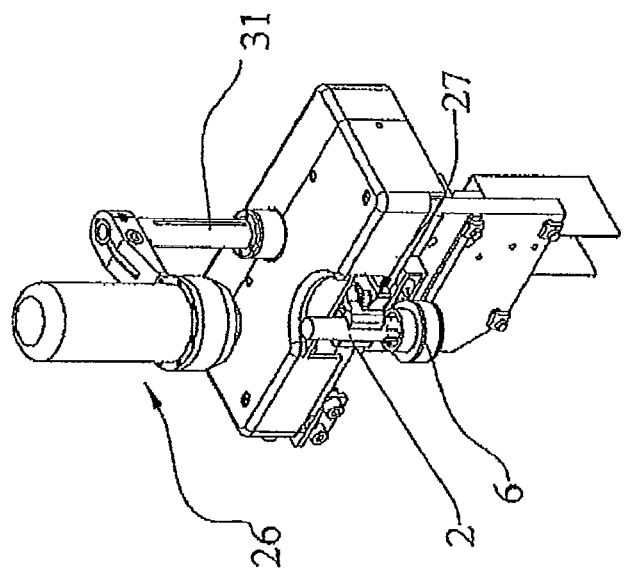
FIG. 6 shows the test tube closing device in a configuration which follows that of FIG. 5.
Figure 5:
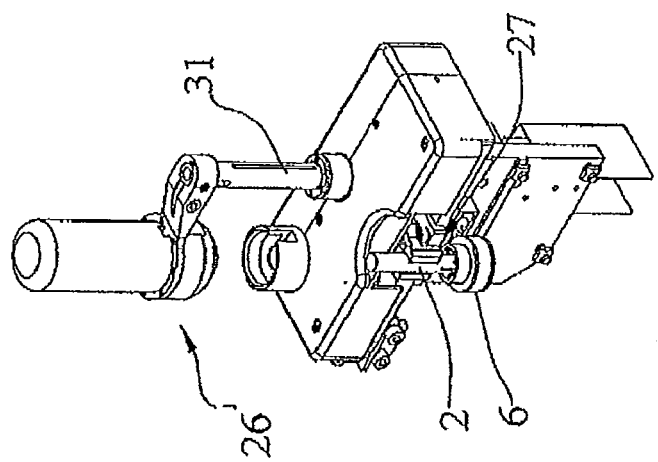
FIG. 5 shows a configuration of the test tube closing device after picking the cap.

When a test tube reaches the working point 7 on the conveyor 1, it is stopped by a stopping device included in the conveyor 1 and the mechanical arms 27 are taken to the closing position (as shown in FIG. 1) to block the test tube 2. The head 26, after a cap 5 has been received as previously described, is raised by means of the ascent/descent device 31 (FIG. 5), and rotates to place itself over the test tube 2 (FIG. 6), to then descend, in virtue of the ascent/descent device 31, onto the test tube, placing itself in the position shown in FIG. 7. When descending towards the test tube 2, the electric motor 30 rotates the chamber 29, which by rotating, in contact with the test tube, engages the thread thus correctly fastening the cap.

The closing device 9 can be provided with a sensor adapted to detect the resistance of the ascent/descent device during the step of descending the head 26 on the test tube, allowing the apparatus to recognize the stroke end and thus the correct fastening of the cap 5 on the test tube 2.

At the end of the process, the test tube 2 closed by an appropriate cap 5, contained in the transporting device 6, may be released and may proceed the process on the conveyor 1, being transported by a conveyor belt 3 towards further processing and testing modules interfacing on the conveyor 1.

Possibly, once closed, the test tube 2 may be unloaded from the conveyor and transported to external test laboratories.

The checks performed by the sensors present at the various actuating points of the described apparatus, coordinated by a control unit, serve the important function of monitoring the correct operation of the apparatus, thus ensuring awareness to the operating devices and preventing operating errors from having severe consequences when processing the test tubes containing biological material.

The described device is thus included in an automation context of the whole working cycle performed on biological material specimens in a test laboratory.

The invention claimed is:
1. An apparatus for automatically closing test tubes with caps, which comprises:
   a test tube closing device,
   a cap sensor disposed in the test tube closing device, and
   a cap recruiting and loading device, said cap recruiting and loading device including:
      a loading chamber,
      a curved channel for transferring caps to said loading chamber in a position reversed from its initial position, a vertically disposed channel member communicating with said loading chamber, a horizontally disposed pusher member adapted to push the cap from said loading chamber into said channel member, said cap sensor being adapted to control the activation of the horizontally disposed pusher, a stem member slidably disposed within said channel member for transferring the cap vertically to the test tube closing device, and sensors adapted to detect the displacement of the stem are disposed in the bottom and top portions of the vertically disposed channel, said sensors cooperating with the horizontally disposed pusher for transferring the caps to said vertically disposed channel, wherein the test tube closing device includes a movable head which is adapted to grip and rotate the cap which was pushed up by the stem member, thereby closing the test tube.

2. The apparatus of claim 1, wherein a sensor is disposed in the curved channel for detecting the presence of caps within said curved channel.

3. The apparatus of claim 1, wherein the movable head is rotatable between a position for receiving the cap to a position for rotatably applying the cap to the test tube.

4. The apparatus of claim 3, wherein resistance means is provided to identify the completion of the closing of the test tube.

* * * * *